United States Patent [19]

Burhop et al.

[11] Patent Number: 5,970,985
[45] Date of Patent: Oct. 26, 1999

[54] USE OF HEMOGLOBIN TO TREAT SYSTEMIC INFLAMMATORY RESPONSE SYNDROME

[75] Inventors: Kenneth E. Burhop, Mundelein, Ill.; Robert J. Przybelski, Fitchburg, Wis.

[73] Assignee: Baxter International, Inc., Deerfield, Ill.

[21] Appl. No.: 08/968,168

[22] Filed: Nov. 12, 1997

Related U.S. Application Data

[63] Continuation-in-part of application No. 08/745,495, Nov. 12, 1996, abandoned.

[51] Int. Cl.$^6$ ..................................................... A61B 19/00
[52] U.S. Cl. ............................................... 128/898; 514/6
[58] Field of Search ................................ 128/898; 514/6, 514/21; 530/385

[56] References Cited

U.S. PATENT DOCUMENTS

| | | |
|---|---|---|
| 4,529,719 | 7/1985 | Tye .............................................. 514/6 |
| 5,295,944 | 3/1994 | Teicher et al. . |
| 5,296,466 | 3/1994 | Kilbourn et al. . |
| 5,334,706 | 8/1994 | Przybelski . |
| 5,344,393 | 9/1994 | Roth et al. . |
| 5,428,007 | 6/1995 | Fischer et al. . |
| 5,451,205 | 9/1995 | Roth et al. . |
| 5,480,866 | 1/1996 | Bonaventura et al. . |
| 5,510,464 | 4/1996 | Przybelski . |
| 5,614,490 | 3/1997 | Przybelski . |

FOREIGN PATENT DOCUMENTS

| | | |
|---|---|---|
| 63-208523 | 8/1988 | Japan . |
| 92/20368 | 11/1992 | WIPO . |
| 92/20369 | 11/1992 | WIPO . |
| 93/16721 | 9/1993 | WIPO . |
| 95/03068 | 2/1995 | WIPO . |

OTHER PUBLICATIONS

Conrad et al. "Effect of Red Cell Transfusion on Oxygen Consumption Following Fluid Resuscitation in Septic Shock" Circ Shock, 31(4): 419–29 (abstract) (Aug. 1990).
Nelson et al. "Synthesis and Properties of Polymerized, Diaspirin Cross–Linked Hemoglobins." Biomaterials, Artificial Cells, and Immobilization Biotechnology 20 (2–4): 253–8 (1992).
Malcolm et al. "Characterization of the Hemodynamic Response to Intravenous Diaspirin Crosslinked Hemoglobin Solution in Rats." Artif. Cells Blood Substit. Immobil. Biotechnol 22(1): 91–107 (Apr., 1994).
Slanetz et al., "Hemoglobin Blood Substitutes in Extended Preoperative Autologous Blood Donation: An Experimental Study," Surgery, vol. 115, No. 2, pp. 246–254, 1994.
Simoni et al., "Cytokines and PAF Release from Human Monocytes and Macrophages: Effect of Hemoglobin and Contaminants" Art. Cells, Blood Subs., and Immob. Biotech. 22(3): 525–534 (1994).
Schultz et al., "Diaspirin Crosslinked Hemoglobin (DCLHb) Attenuates Bacterial Translocation in Rats" Art. Cells, Blood Subs., and Immob. Biotech. 23(6): 647–664 (1995).

Otterbein et al., "Hemoglobin Provides Protection Against Lethal Endotoxemia in Rats: The Role of Heme Oxygenase–1," Am. J. Respir. Cell Mol. Biol., vol. 13, pp. 595–601, 1995.
Swan et al. "Pharmacologic Profile of Diaspirin Cross–Linked Hemoglobin in Hemodialysis Patients." Am. J. Kidney Dis. 26(6):918–23 (Dec. 1995).
Soltero et al. "Diaspirin Crosslinked Hemoglobin (DCLHb) May Be Beneficial in the Treatment of Septic Shock" Suppl to Shock; 3 (abstract #192) (1995).
Lin et al. "Development of a Model to Study Gastrointestinal Oxygen Utilization in Sepsis: Preliminary Results" Artif. Cells Blood Subs. Immobil. Biotech. 24(4):382 (abstract) (1996).
d'Almeida et al. "Influence of Sepsis on the Pharmacokinetics of Diaspirin Crosslinked Hemoglobin in Rats" Artif. Cells Blood Subs. Immobil Biotech. 24(4): 299 (abstract) (1996).
Law et al. "Diaspirin Crosslinked Hemoglobin Improves Perfusion in Sepsis" Artif Cells Blood Subs Immobil Biotech 24(4):377 (abstract) (1996).
Sielenkamper et al. "Efficacy of Diaspirin Crosslinked Hemoglogin, Fresh Blood and Old Blood Transfusion in Oxygen Supply–Dependent Septic Rats" Artif. Cells Blood Subs Immobil Biotech, 24(4):426 (abstract) (1996).
Sielenkamper et al. "Diaspirin Crosslinked Hemoglobin Improves Small Bowel Microvascular Blood Flow in Septic Rats" Int. Care Med.; 22(suppl 3): S440 (abstract #72) (1996).
d'Almeida et al. "Pharmacokinetics of Diaspirin Cross–Linked Hemoglobin in a Model of Sepsis in the Rat" Crit. Care Med. 24(1): A27 (abstract) (1996).
Mourelatos et al. "The Effects of Diaspirin Cross–Linked Hemoglobin in Sepsis." Shock 5(2): 141–148 (1996).
Alayash, "Hemoglobin and Tissue Oxidants: Physiological Implications and Protective Strategies," Artificial Cells, Blood Substitutues, and Immobilization Biotechnology, vol. 24, No. 4, p. 298, (abstract), 1996.
Garrioch et al., "The Hemodynamic Effects of Diaspirin Cross–Linked Hemoglobin (DCLHb) in the Operative Setting," Critical Care Medicine, vol. 24, No. 1, p. A39 (abstract), 1996.
Rhea et al., "Vasopressor Effects of Diaspirin Cross–Linked Hemoglobin (DCLHb) in Critically Ill Patients," Critical Care Medicine, vol. 24, No. 1, p. 3 (abstract), 1996.

(List continued on next page.)

*Primary Examiner*—Mickey Yu
*Assistant Examiner*—Kelly O'Hara
*Attorney, Agent, or Firm*—Senniger, Powers, Leavitt & Roedel

[57] ABSTRACT

A method for treating systemic inflammatory response syndrome in a mammal by administering to the mammal a hemoglobin preparation after the mammal is diagnosed as suffering from systemic inflammatory response syndrome, wherein the systemic inflammatory response syndrome is a condition other than sepsis.

24 Claims, No Drawings

OTHER PUBLICATIONS

Simoni et al., "Immunohistochemical Evaluation of Adhesion Molecules and Von Willebrand Factor Expression in Human Coronary Artery Endothelial Cells Incubated with Different Hemoglobin Solutions," Artificial Cells, Blood Substitutes, and Immobilization Biotechnology, vol. 24, No. 4, p. 428 (abstract), 1996.

Simoni et al., "Modified Hb Solution, with Low Prooxidant Potential and Desired Pharmacological and Anti–Inflammatory Properties, Does Not Activate the Transcription Factor NF–kappa B in Human Vascular Endothelial Cells," Artificial Cells, Blood Substitutes, and Immobilization Biotechnology, vol. 24, No. 4, p. 429, (abstract), 1996.

Vercellotti, "Vascular Responses to Hemoglobin Derived Iron: Potential Dangers and Cytoprotective Adaptations," Artificial Cells, Blood Substitutes, and Immobilization Biotechnology, vol. 24, No. 4, p. 451, (abstract), 1996.

Nelson et al. "Synthesis and Properties of Polymerized, Diaspirin Cross–Linked Hemoglobins." Biomaterials, Artificial Cells, and Immobilization Biotechnology 20 (2–4): 253–8 (1992).

Malcolm et al. "Characterization of the Hemodynamic Response to Intravenous Diaspirin Crosslinked Hemoglobin Solution in Rats." Artif. Cells Blood Substit. Immobil. Biotechnol 22(1): 91–107 (Apr., 1994).

Swan et al. "Pharmacologic Profile of Diaspirin Cross–Linked Hemoglobin in Hemodialysis Patients." Am. J. Kidney Dis. 26(6):918–23 (Dec. 1995).

Mourelatos et al. "The Effects of Diaspirin Cross–Linked Hemoglobin in Sepsis." Shock 5(2): 141–148 (1996).

USE OF HEMOGLOBIN TO TREAT SYSTEMIC INFLAMMATORY RESPONSE SYNDROME

REFERENCE TO RELATED APPLICATIONS

This application is a continuation-in-part application of U.S. Ser. No. 08/745,495 filed Nov. 12, 1996 now abandoned.

BACKGROUND OF THE INVENTION

The present invention relates to the prevention of sepsis and the treatment of systemic inflammatory response syndrome. More specifically, the present invention relates to the prophylactic use of a hemoglobin preparation to reduce the severity of, or to prevent, sepsis in patients recognized to be at risk for developing sepsis. The invention also relates to the therapeutic use of a hemoglobin preparation to treat systemic inflammatory response syndrome in patients diagnosed as suffering from systemic inflammatory response syndrome.

A systemic inflammatory response can be observed after a patient suffers an infectious or noninfectious insult. If the inflammatory response results from a noninfectious cause, the response is generally known as systemic inflammatory response syndrome. A frequent complication of the syndrome is organ dysfunction. Inflammatory responses resulting from infection are generally defined as sepsis (ACCP/SCCM (1992), *Critical Care Medicine,* 20(5):864–874).

Sepsis results from acute invasion of the bloodstream or other tissues by pathogenic microorganisms or toxic products thereof, such as bacterial endotoxins. Sepsis is often caused by infection with bacteria, pathogenic viruses, fungi, or protozoa. Sepsis resulting from infection can be clinically diagnosed by positive blood cultures. Additional clinical evidence suggestive of infection or a systemic response to infection is evident as sepsis progresses. This clinical evidence includes tachypnea, tachycardia, and hyperthermia or hypothermia, followed by abnormal lactate levels, oliguria, obtundation and other signs of altered organ perfusion normally associated with incipient septic shock. Early stage septic shock is manifested by hypotension that lasts for less than one hour and which is responsive to conventional therapy such as intravenous fluid administration or pharmacologic intervention. Refractory septic shock can be diagnosed by hypotension that lasts for more than one hour despite adequate volume resuscitation and that requires the use of vasopressors or higher doses of dopamine (Bone (1991) *Ann. Int. Med.* 115:457–469). Multiorgan failure can occur as or after a patient suffers septic shock.

Sepsis and subsequent multiple system organ failure (MSOF) are a major cause of late morbidity and mortality in trauma victims (Carrico et al. (1986) *Arch. Surg.* 121:196–208; Goris et al. (1985) *Arch. Surg.* 120:1109–1115; Fine et al. (1959) *N. Engl. J. Med.* 260:214–220; Rush (1989) *Ann. Surg.* 210:342–347). In more than 30% of bacteremic trauma patients dying of sepsis and its sequelae, no focus of infection can be identified either clinically or at autopsy. While clinical studies have so far failed to establish a cause and effect relationship between gut failure and systemic sepsis or MSOF, the infection of these patients with bacteria normally found within the gastrointestinal tract has led many clinicians and scientists to hypothesize that these infections originated in the gut (Deitch (1990) *Arch. Surg.* 125:403–404; Livingston (1993) *Am. J. Surg.* 165:8S–13S; Sori et al. (1988) *Am. J. Surg.* 155:187–192; Wilmore et al. (1988) *Surgery* 104:917–923; Zhi-Yong et al. (1992) *J. Trauma* 32:148–153).

Hemoglobin has been administered to increase perfusion, and increase blood pressure from abnormally low levels, in patients experiencing septic shock (U.S. Pat. No. 5,334,706), to protect against endotoxic shock when administered to rats at a concentration of 300 mg/kg body weight before inducing endotoxic shock (Otterbein et al. (1995) *Amer. J. Resp. Cell Mol. Bio.* 13:595–601), and for prophylaxis or treatment of septic shock induced by internal nitric oxide production at a hemoglobin concentration of 100–10,000 mg/kg body weight (U.S. Pat. No. 5,296,466).

Current experimental approaches to treating septic shock employ monoclonal antibodies against endotoxin components and TNF, and the use of platelet-activating factor antagonists (Stone (1994) *Science* 264:365–367). Mortality due to septic shock varies from 20 to 60% despite the use of antibiotics and intensive supportive care (Bone et al. (1987) *N. Engl. J. Med.* 317:653–658; Kreger et al. (1980) *Am. J. Med.* 68:344–355; The Veterans Administration Systemic Sepsis Cooperative Study Group (1987) *N. Engl. J. Med.* 317:659–665).

A need therefore exists for agents effective in preventing or reducing the severity of sepsis in mammals. Agents for treating systemic inflammatory response syndrome in mammals are also needed.

SUMMARY OF THE INVENTION

Among the objects of the present invention, therefore, may be noted the provision of a hemoglobin solution for preventing sepsis in a mammal or for treating systemic inflammatory response syndrome in a mammal, and the provision of methods therefor.

The present invention provides a method for reducing the severity of or preventing sepsis in a patient recognized to be risk for developing sepsis, by administering an effective amount of a hemoglobin preparation before sepsis develops in the patient.

The present invention also provides a method for treating systemic inflammatory response syndrome in a mammal, by administering an effective amount of a hemoglobin preparation to the mammal after the mammal is diagnosed as suffering from systemic inflammatory response syndrome.

Further scope of the applicability of the present invention will become apparent from the detailed description provided below. However, it should be understood that the following detailed description and examples, while indicating preferred embodiments of the invention, are given by way of illustration only since various changes and modifications within the spirit and scope of the invention will become apparent to those skilled in the art from this detailed description.

DETAILED DESCRIPTION OF THE INVENTION

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

The contents of each of the references cited herein are herein incorporated by reference in their entirety.

The present method provides a prophylactic means for preconditioning a patient recognized to be at risk for developing sepsis by administering a hemoglobin preparation thereto so as to prevent the development of sepsis, or to reduce the severity of sepsis that may develop in the patient.

As used herein, the term "sepsis" is any condition associated with the presence of pathogenic microorganisms or their toxins in the blood or other tissues of a patient. The term "sepsis" includes bacteremia and various stages of septic shock, such as sepsis syndrome, incipient septic shock, early septic shock, and refractory septic shock (Bone (1991) *Ann. Int. Med.* 115:457–469).

The present invention also provides a therapeutic means of treating a patient diagnosed as suffering from systemic inflammatory response syndrome by administering a hemoglobin preparation to the patient after the patient has been diagnosed.

As used herein, the term "systemic inflammatory response syndrome" is any condition associated with a systemic inflammatory response, which results from a noninfectious insult, in which the patient exhibits at least two of the following manifestations: a) a body temperature greater than 38° C. or less than 36° C.; b) a heart rate greater than 90 beats per minute; c) tachypnea, as manifested by a respiratory rate of greater than 20 breaths per minute or hyperventilation, as indicated by a $Paco_2$ less than 32 torr (less than 4.3 kPa); d) an alteration of the white blood cell count of greater than 12,000 cells/mm$^3$, less than 4,000 cells/mm$^3$, or the presence of greater than 10% immature neutrophils (band forms). The term "systemic inflammatory response syndrome" does not include sepsis or any other inflammatory response caused by an infectious process. See ACCP/SCCM (1992), *Critical Care Medicine*, 20(5): 864–874 for further definition of systemic inflammatory response syndrome and sepsis as considered by the American College of Chest Physicians and the Society of Critical Care Medicine.

In the present invention, a hemoglobin preparation is administered in an effective amount to a mammal, including a human patient, at risk for developing sepsis or diagnosed as suffering from systemic inflammatory response syndrome. Patients likely to develop sepsis, for example, include those who have suffered a trauma, accident, disease, puncture wound, or gastrointestinal injury, or patients that will undergo or have undergone hemodialysis, surgery, or invasive procedures such as catheterization or intubation. Patients who have developed an infection which has not progressed to sepsis are also at risk for developing sepsis. Severely ill patients in intensive-care units or cardiac-care units, or immunocompromised patients, are generally at risk for developing sepsis as well. The beneficial effects resulting from hemoglobin administration include a reduction in severity or the prevention of sepsis in such patients.

Useful doses of hemoglobin for the prophylactic treatment of sepsis or for the therapeutic treatment of systemic inflammatory response syndrome according to the present invention are those that are effective in reducing or preventing conditions associated with sepsis or systemic inflammatory response syndrome, such as bacteremia, tachypnea, tachycardia, hyperthermia, hypothermia, altered organ perfusion, abnormal lactate levels, oliguria, cyanosis, obtundation, hypotension and multiorgan failure.

These results can be achieved with hemoglobin doses effective in reducing or preventing the symptoms listed above, preferably in the range of from about 5.0 mg/kg body weight to about 90 mg/kg body weight, more preferably from about 10 mg/kg body weight to about 80 mg/kg body weight, and most preferably from about 20 mg/kg body weight to about 70 mg/kg body weight.

Administration of an effective amount of hemoglobin to reduce or eliminate the onset of sepsis or treat systemic inflammatory response syndrome by the methods of the present invention can be carried out parenterally, for example by intravenous or intraarterial injection, infusion, or arterial cannulization (in appropriate clinical circumstances), pretraumatically or preoperatively. Such effective amount can be administered in a single dose, or in a series of multiple subdoses. The single dose or each of said multiple subdoses can be administered by slow continuous infusion.

Administration of hemoglobin to prevent or reduce sepsis can be via such single dose, or multiple subdoses, given within about 72 hours minutes to about 12 hours prior to hemodialysis, surgery, an invasive medical procedure or other scheduled procedure, more preferably within about 48 hours to about 18 hours, most preferably within about 36 hours to about 24 hours prior thereto. If a patient suffers an accident, puncture wound, gastrointestinal injury, or other trauma, or has been admitted to an intensive-care unit or cardiac-care unit of a hospital, the hemoglobin is administered immediately upon admission or diagnosis, or as soon as practicable. Hemoglobin is also administered upon diagnosis or as soon as practicable to a patient diagnosed as being immunocompromised or as having an infection other than sepsis, or to a patient diagnosed as suffering from systemic inflammatory response syndrome.

As used herein, the term "hemoglobin" includes all oxygen-carrying proteins containing globin or globin-like polypeptides and heme, and being capable of transporting and releasing oxygen to cells, tissues or organs when introduced into the blood stream of a mammal in a physiologically compatible carrier. The term "hemoglobin" includes all naturally- and non-naturally-occurring hemoglobin. The term "hemoglobin preparation" includes hemoglobin in a physiologically compatible carrier or lyophilized hemoglobin reconstituted with a physiologically compatible carrier, but does not include whole blood, red blood cells or packed red blood cells.

Naturally-occurring hemoglobin includes any hemoglobin identical to hemoglobin naturally existing within a cell. Naturally-occurring hemoglobin is predominantly wild-type hemoglobin, but also includes naturally-occurring mutant hemoglobin. Wild-type hemoglobin is hemoglobin most commonly found within natural cells. Wild-type human hemoglobin includes hemoglobin A, the normal adult human hemoglobin having two α- and two β-globin chains. Mutant hemoglobin has an amino-acid sequence that differs from the amino-acid sequence of wild-type hemoglobin as a result of a mutation, such as a substitution, addition or deletion of at least one amino acid. Adult human mutant hemoglobin has an amino-acid sequence that differs from the amino-acid sequence of hemoglobin A. Naturally-occurring mutant hemoglobin has an amino-acid sequence that has not been modified by humans. The naturally-occurring hemoglobin of the present invention is not limited by the methods by which it is produced. Such methods typically include, for example, erythrocytolysis and purification, recombinant production, and protein synthesis.

Non-naturally-occurring hemoglobin includes mutant hemoglobin having an amino-acid sequence different from the amino-acid sequence of hemoglobin naturally existing within a cell, and chemically-modified hemoglobin. Such non-naturally-occurring mutant hemoglobin is not limited by its method of preparation, but is typically produced using one or more of several techniques known in the art, including, for example, recombinant DNA technology, transgenic DNA technology, protein synthesis, and other mutation-inducing methods.

Chemically-modified hemoglobin is a natural or non-natural hemoglobin molecule which is bonded to or encapsulated by another chemical moiety. For example, a hemoglobin molecule can be bonded to pyridoxal-5'-phosphate, or other oxygen-affinity-modifying moiety to change the oxygen-binding characteristics of the hemoglobin molecule, to crosslinking agents to form crosslinked or polymerized hemoglobin, or to conjugating agents to form conjugated hemoglobin. Conjugated, polymerized and crosslinked hemoglobins generally exhibit longer intravascular retention times than unmodified hemoglobin.

Several examples of hemoglobin modification technology which can be used in the practice of the present invention have been described in the scientific literature (reviewed by R. M. Winslow (1992) in *Hemoglobin-Based Red Cell Substitutes*, The Johns Hopkins University Press, Baltimore, Md.). Some representative methods of preparing chemically-modified hemoglobin for use in the invention are described below.

Hemoglobin can be modified to improve its oxygen-binding affinity. Reagents that bind to the 2,3-diphosphoglycerate binding site of a hemoglobin molecule, reduce the oxygen affinity of the hemoglobin molecule, and prolong intravascular retention are described in U.S. Pat. Nos. 4,529,719 and 5,380,824 (pyridoxal-5'-phosphate), U.S. Pat. No. 4,600,531 (carboxyl-, phosphonate-, phosphate-, sulfonate- or sulfate-phenyl ester-containing compounds such as mono(3,5-dibromosalicyl)fumarate), U.S. Pat. No. 5,268,500 (arylureido acid compound), U.S. Pat. No. 5,382,680 (2[4-(((benzyl)amino)carbonyl) phenoxy]-2-methyl propionic acids), and U.S. Pat. Nos. 5,290,803 and 5,432,191. In general, any method of preparing or modifying hemoglobin such that the hemoglobin can transport and release oxygen is suitable in the present method. Preferably, the hemoglobin has a $P_{50}$ of between about 20 and about 45 mm Hg.

An encapsulated hemoglobin is hemoglobin surrounded by a material which retains the hemoglobin within the material yet allows smaller molecules to pass through the material to react with hemoglobin and reaction products to pass out of the material. Materials for encapsulating hemoglobin are described in U.S. Pat. No. 4,343,715 (polyurethane, acrylic gels, maleic anhydride polymers, epoxy polymers, glutaronic aldehyde polymers), U.S. Pat. Nos. 5,061,688, 5,217,648 and 5,438,041 (oil emulsion), and U.S. Pat. Nos. 4,322,311, 4,324,683 and 4,390,521 (polymers).

A conjugated hemoglobin is at least one non-hemoglobin molecule covalently or ionically bound to a hemoglobin. In some embodiments, the non-hemoglobin molecule can also form an intermolecular crosslink between hemoglobin molecules. Conjugating materials and methods for preparing hemoglobin conjugates are described in WO 91/07190 (polyalkylene glycol), U.S. Pat. Nos. 4,670,417, 5,091,176, 5,219,564, 5,234,903, 5,312,808 and 5,386,014, WO 94/04193, WO 94/09027 and Japanese Patent Nos. 59-104323 and 61-053223 (polyalkylene oxide), U.S. Pat. Nos. 5,349,001 and 5,405,877 (cyclic imide thione activated polyalkylene oxide), U.S. Pat. No. 4,301,144 (polyalkylene glycol, alkylene glycol copolymers, alcohol-polyalkylene glycol ether copolymers, carboxylic acid-polyalkylene glycol ester copolymers, and amine-polyalkylene glycol derivatives), U.S. Pat. Nos. 4,267,234, 4,267,435 and 4,369,226 (polyglutaraldehyde), Canadian Patent Application No. 2,074,852 (divinyl sulfone), U.S. Pat. No. 4,412,989 (polyether), U.S. Pat. No. 4,377,512 (inulin), U.S. Pat. Nos. 5,079,337 and 5,110,909 (polysaccharide, polyvinyl alcohol, polyvinyl pyrrolidone, polymethacrylate, polypeptide, polyalkylene glycol, hydroxyalkyl starch, and dextran), U.S. Pat. No. 4,920,194 (sulfated glycosaminoglycan fragments, such as heparin), U.S. Pat. No. 4,970,156 (active protein), U.S. Pat. No. 4,336,248 (dialdehyde), U.S. Pat. No. 4,900,780 (hydroxyethyl starch or tetronic polymer), and U.S. Pat. Nos. 4,698,387, 4,935,465, and 5,514,780.

Crosslinked hemoglobin is intramolecularly linked between globin or globin-like protein subunits by a crosslinking agent. A subunit is one globin or globin-like protein of a hemoglobin molecule. Intramolecular crosslinking prevents dissociation of globin or globin-like proteins when hemoglobin is administered in vivo. Hemoglobin A, for example, can dissociate into two $\alpha$-$\beta$ globin dimers if the dimers are not crosslinked. Crosslinked hemoglobins and methods for their preparation are described in U.S. Pat. Nos. 4,529,719 and 4,600,531 ($\alpha$-$\alpha$ linkage using diphenyl ester derivatives such as bis(3,5-dibromosalicyl)fumarate), U.S. Pat. Nos. 4,001,401 and 4,053,590 ($\alpha$-$\beta$ globin linkage using halogenated cycloalkanes, diepoxides, and diazobenzidines), U.S. Pat. No. 4,857,636 (aldehyde derived from oligosaccharide), U.S. Pat. No. 5,334,705 (benzenetricarboxylate), WO 94/21682 ($\beta$-$\beta$ globin linkage using di- or trisaccharide), U.S. Pat. No. 5,290,919 and 5,387,672 (di- or trivalent compounds), U.S. Pat. No. 5,334,707 ($\beta$-$\beta$ or $\alpha$-$\alpha$ linkage using acyl phosphate ester), U.S. Pat. No. 5,362,885 and WO 92/09630 (imidoesters, such as dimethyl adipimidate or dimethyl suberimidate), U.S. Pat. No. 5,514,780 (polycarboxylic acid), U.S. Pat. No. 5,399,671 and WO 90/13309 ($\beta$-$\beta$ linkage), and U.S. Pat. No. 4,473,496 (dialdehyde).

A polymerized hemoglobin is intermolecularly linked between hemoglobin molecules. Polymerization generally increases the molecular weight of the hemoglobin, which improves its intravascular half-life. Polymerization agents for preparing polymerized hemoglobin are described in pending U.S. applications Ser. Nos. 08/149,679, 08/173,882, 08/480,593, and 08/473,459, U.S. Pat. No. 4,777,244 (aliphatic dialdehyde), U.S. Pat. No. 5,349,054 (benzenepentacarboxylate), WO 94/14460 (transglutaminase), and EP 201618 (glutaraldehyde).

Hemoglobins can also be modified by a combination of the methods described above, for example, as described in Japanese Pat. Nos. 59-089629, 59-103322, and 59-104323 (pyridoxal-5'-phosphate modification and polyethylene glycol conjugation of hemoglobin), U.S. Pat. No. 5,248,766 (crosslinking and polymerization of tetrameric hemoglobins with oxiranes), U.S. Pat. Nos. 4,650,786, 4,710,488 and 4,900,816 (inositol phosphate aldehyde modification and polysaccharide conjugation of hemoglobin), U.S. Pat. Nos. 5,189,146 and 5,364,932 (di- or polyaldehydes for intra- and intermolecular crosslinking), EP 361719 (pyridoxylation, dicarboxylic acid halo-ester crosslinking, and polymerization), WO 90/13309 (pyridoxal-5-phosphate derivative for intramolecular crosslinking and glutaraldehyde for polymerization), U.S. Pat. No. 5,439,882 (periodate-oxidized ATP intramolecular crosslinking and periodate-oxidized adenosine polymerization), U.S. Pat. Nos. 4,826,811 and 5,194,590 (pyridoxylation and glutaraldehyde polymerization), and U.S. Pat. No. 4,529,719 (intramolecularly crosslinked with diaspirin ester and pyridoxylated).

Recombinantly-produced hemoglobin is produced by recombinant DNA methodologies, for example, by sitedirected mutagenesis, gene fusion, or transfecting a genetically engineered plasmid into a microorganism such as a bacterium or yeast, a cultured cell such as an insect cell, a mammalian cell, or plant cell, a transgenic plant, a transgenic animal, or any other host cell or organism, where the plasmid includes a nucleic acid polymer (e.g., cDNA) which encodes a globin protein, a fusion protein, or a protein similar to globin that can reversibly bind oxygen. Recombinant mutant and artificial hemoglobins and their production in cell cultures or fluids is described in U.S. Pat. Nos. 5,449,759 and 5,028,588, and in WO 88/09179, AU 614525, GB 2234749 B, and EP 358708 B1. Di-α and di-β globin-like polypeptides and other hemoglobin variants produced in bacteria and yeast, and other fused hemoglobins, are described in WO 90/13645, WO 91/16349, EP 561245 A1, and AU 614525. Non-natural multimeric hemoglobin-like proteins are described in WO 93/09143. Production and recovery of human hemoglobin from transgenic pigs are described in WO 92/22646, WO 93/25071, and WO 95/04744. Methods for the preparation and purification of hemoglobin derived from erythrocyte and non-erythrocyte cells are described in WO 92/22646, WO 93/25071, WO 95/04744, WO 95/14038, and WO 96/15151.

Hemoglobins useful in the methods of the present invention are also free of pyrogens, toxins and other contaminants. Pyrogen-free hemoglobin is hemoglobin that is absolutely free of fever-producing contaminants, or hemoglobin that contains amounts of fever-producing contaminants that are physiologically acceptable to patients to which the hemoglobin will be administered. Bacterial endotoxins contaminate hemoglobin derived from erythrocytes. The endotoxins are released when erythrocytes are disrupted to obtain hemoglobin. Recombinant hemoglobin produced in non-erythrocyte host cells such as bacteria can also become contaminated with cellular components such as proteins, toxins, or polysaccharides that can elicit toxic or pyrogenic responses when administered to mammals (Rietschel et al. (1992) *Scientific American* 267:54–61; Suffredini et al. (1989) *New Eng. J. Med.* 321:280–287).

Hemoglobins for use in the present invention are also stroma-free. Stroma, the insoluble cell membrane fragments that contaminate hemoglobin derived from lysed erythrocytes, is toxic and has been reported to cause dyspnea, bronchospasm, hypotension, arrhythmia, disseminated intravascular coagulation, activation of complement, and renal, myocardial, and hepatic changes associated with ischemia and acute inflammation (Feola (1988) *Surgery, Gynecology & Obstetrics* 166:211–222; MacDonald et al. (1988) *F.A.S.E.B. J.* 2(6) Abstr. 8217; Stone et al. (1979) *Surgery, Gynecology & Obstetrics* 149:874–876; Rabiner et al. (1967) *J. Exp. Med.* 126:1127–1142. For purposes of the present invention, "stroma-free hemoglobin" is hemoglobin, as defined herein, which is either absolutely free of stroma, or which contains stroma at concentrations that are physiologically acceptable (i.e., do not cause adverse side effects) in a patient. Stroma-free hemoglobin that is absolutely free of stroma includes recombinant hemoglobin produced in a non-erythrocyte. Stroma-free hemoglobin that contains stroma at physiologically acceptable levels includes, for example, purified hemoglobin derived from erythrocytes.

The hemoglobin can be dialyzed or exchanged by ultrafiltration into a physiologically acceptable solution preferably to between about 1 and about 20 g/dl hemoglobin. The solution generally comprises a physiologically compatible electrolyte vehicle isosmotic with whole blood and which maintains the reversible oxygen-carrying and delivery properties of the hemoglobin. The physiologically acceptable solution can be, for example, physiological saline, a saline-glucose mixture, Ringer's solution, lactated Ringer's solution, Locke-Ringer's solution, Krebs-Ringer's solution, Hartmann's balanced saline, heparinized sodium citrate-citric acid-dextrose solution, and polymeric plasma substitutes, such as polyethylene oxide, polyvinyl pyrrolidone, polyvinyl alcohol and ethylene oxide-propylene glycol condensates. Such solutions can be administered parenterally, for example by intravenous or intraarterial injection or infusion, without adverse side effects. The hemoglobin can also be lyophilized for storage and reconstituted prior to use. Methods for preparing such solutions or lyophilized powders are known in the art.

A preferred hemoglobin for use in the present method is hemoglobin crosslinked with bis(3,5-dibromosalicyl) fumarate to create a fumarate crosslink between the two α subunits (DCLHb™, manufactured by Baxter Healthcare, Deerfield, Ill.). This crosslinked hemoglobin is more fully described, together with methods for its preparation, in U.S. Pat. Nos. 4,598,064, 4,600,531, and RE 34,271, omitting the chromatography step. This hemoglobin is preferably manufactured under the conditions disclosed in U.S. Pat. Nos. 4,831,012, 4,861,867, 5,128,452 and 5,281,579 and U.S. patent application Ser. No. 07/207,346.

In practice, a preferred DCLHb™ solution, manufactured by Baxter Healthcare Corporation and useful in the present invention, contains 10 g/dl of modified tetrameric hemoglobin in a balanced electrolyte solution. The product is prepared from units of human red cells from volunteer donors which have been tested and found negative for HbsAg, HIV-1 and 2, and HCV. During manufacture, the red cells are osmotically lysed to release hemoglobin. After ultrafiltration, the stroma-free hemoglobin is reacted with the diaspirin crosslinking agent to produce a stabilized tetrameric hemoglobin having a fumaryl moiety linking the two α subunits. After crosslinking, the reaction mixture is heated to effect viral deactivation and precipitate extraneous proteins. The precipitate is removed by filtration. The DCLHb™ is then concentrated and diafiltered into a physiologic electrolyte vehicle. The resulting solution is isosmotic with whole blood, hyperoncotic (approximately 40 torr), and has the composition shown in Table 1.

TABLE 1

| Chemical Assay of 10% Diaspirin Crosslinked Hemoglobin Solution | |
|---|---|
| Hemoglobin content | 10 g/dl |
| Oncotic pressure | 43 mm Hg |
| Osmolarity | 290 mOsm/L |
| pH | 7.4 @ 37° C. |
| Na$^+$ | 145 mEq/L |
| K$^+$ | 4 mEq/L |
| Ca$^{++}$ | 2.3 mEq/L |
| Mg$^{++}$ | 0.9 mEq/L |
| Cl$^-$ | 115 mEq/L |
| Lactate | 34 mEq/L |

The invention being thus described, it will be obvious that the same can be varied in many ways. Such variations are not to be regarded as a departure from the spirit and scope of the present invention, and all such modifications and equivalents as would be obvious to one skilled in the art are intended to be included within the scope of the following claims.

What is claimed is:

1. A method of treating systemic inflammatory response syndrome in a mammal, comprising administering to said mammal a hemoglobin preparation containing from about 5.0 milligrams hemoglobin per kilogram body weight to about 90 milligrams hemoglobin per kilogram body weight after said mammal is diagnosed as suffering from systemic inflammatory response syndrome, wherein the systemic inflammatory response syndrome is a condition other than sepsis.

2. The method of claim 1 wherein said administering is carried out as soon as practicable after the patient is diagnosed as suffering from systemic inflammatory response syndrome.

3. The method of claim 1 wherein said hemoglobin preparation is a solution containing hemoglobin that has been chemically modified to prevent intramolecular dissociation or to increase intravascular persistence.

4. The method of claim 1 wherein said hemoglobin exhibits an oxygen binding affinity within a range of $P_{50}$ values between about 20 and about 45 mm Hg.

5. The method of claim 1 wherein said hemoglobin is selected from the group consisting of crosslinked hemoglobin, conjugated hemoglobin, encapsulated hemoglobin, and polymerized hemoglobin.

6. The method of claim 5 wherein said crosslinked hemoglobin is diaspirin-crosslinked hemoglobin.

7. The method of claim 1 wherein said hemoglobin preparation contains from about 10 milligrams hemoglobin per kilogram body weight to about 80 milligrams hemoglobin per kilogram body weight.

8. The method of claim 1 wherein said hemoglobin preparation contains from about 20 milligrams hemoglobin per kilogram body weight to about 70 milligrams hemoglobin per kilogram body weight.

9. The method of claim 1 wherein said hemoglobin preparation is in the form of a physiologically acceptable solution for parenteral administration.

10. The method of claim 9 wherein said physiologically acceptable solution contains from about 1 g/dl to about 20 g/dl hemoglobin.

11. The method of claim 1 wherein said hemoglobin preparation is administered in a single dose, or in a series of multiple subdoses.

12. The method of claim 1 wherein the hemoglobin is recombinantly produced.

13. A method of treating systemic inflammatory response syndrome in a human, comprising administering to said human a hemoglobin preparation containing from about 5.0 milligrams hemoglobin per kilogram body weight to about 90 milligrams hemoglobin per kilogram body weight after said human is diagnosed as suffering from systemic inflammatory response syndrome, wherein the systemic inflammatory response syndrome is a condition other than sepsis.

14. The method of claim 12 wherein said administering is carried out as soon as practicable after the human is diagnosed as suffering from systemic inflammatory response syndrome.

15. The method of claim 12 wherein said hemoglobin preparation is a solution containing hemoglobin that has been chemically modified to prevent intramolecular dissociation or to increase intravascular persistence.

16. The method of claim 12 wherein said hemoglobin exhibits an oxygen binding affinity within a range of $P_{50}$ values between about 20 and about 45 mm Hg.

17. The method of claim 12 wherein said hemoglobin is selected from the group consisting of crosslinked hemoglobin, conjugated hemoglobin, encapsulated hemoglobin, and polymerized hemoglobin.

18. The method of claim 17 wherein said crosslinked hemoglobin is diaspirin-crosslinked hemoglobin.

19. The method of claim 12 wherein the hemoglobin is recombinantly produced.

20. The method of claim 12 wherein said hemoglobin preparation contains from about 10 milligrams hemoglobin per kilogram body weight to about 80 milligrams hemoglobin per kilogram body weight.

21. The method of claim 12 wherein said hemoglobin preparation contains from about 20 milligrams hemoglobin per kilogram body weight to about 70 milligrams hemoglobin per kilogram body weight.

22. The method of claim 12 wherein said hemoglobin preparation is in the form of a physiologically acceptable solution for parenteral administration.

23. The method of claim 22 wherein said physiologically acceptable solution contains from about 1 g/dl to about 20 g/dl hemoglobin.

24. The method of claim 12 wherein said hemoglobin preparation is administered in a single dose, or in a series of multiple subdoses.

* * * * *

UNITED STATES PATENT AND TRADEMARK OFFICE
CERTIFICATE OF CORRECTION

PATENT NO. : 5,970,985
DATED : October 26, 1999
INVENTOR(S) : Kenneth E. Burhop et al.

It is certified that error appears in the above-identified patent and that said Letters Patent is hereby corrected as shown below:

Column 10, claim 14, line 7, "claim 12" should read ---claim 13---.
Column 10, claim 15, line 11, "claim 12" should read ---claim 13---.
Column 10, claim 16, line 16, "claim 12" should read ---claim 13---.
Column 10, claim 17, line 19, "claim 12" should read ---claim 13---.
Column 10, claim 19, line 25, "claim 12" should read ---claim 13---.
Column 10, claim 20, line 27, "claim 12" should read ---claim 13---.
Column 10, claim 21, line 31, "claim 12" should read ---claim 13---.
Column 10, claim 22, line 35, "claim 12" should read ---claim 13---.
Column 10, claim 24, line 41, "claim 12" should read ---claim 13---.

Signed and Sealed this

Eighth Day of August, 2000

Attest:

*Attesting Officer*

Q. TODD DICKINSON
*Director of Patents and Trademarks*